United States Patent [19]

Murray

[11] Patent Number: 5,746,905

[45] Date of Patent: May 5, 1998

[54] COATING EVALUATION SYSTEM

[75] Inventor: John N. Murray, Timonium, Md.

[73] Assignee: The United States of America as represented by the Secretary of the Navy, Washington, D.C.

[21] Appl. No.: 601,272

[22] Filed: Feb. 14, 1996

[51] Int. Cl.$^6$ .......................... G01N 27/02; G01N 27/26
[52] U.S. Cl. ................. 205/791; 205/776.5; 324/699; 324/709
[58] Field of Search ..................... 205/791, 776.5; 324/671, 683, 699, 709, 716

[56]     References Cited

U.S. PATENT DOCUMENTS 4,806,849  2/1989  Kihira et al. .................. 324/65 CR
5,093,626  3/1992  Baer et al. ..................... 324/671
5,236,564  8/1993  Berg et al. ..................... 204/181.1
5,373,734  12/1994 Shih et al. ..................... 73/150 R

*Primary Examiner*—Kathryn L. Gorgos
*Assistant Examiner*—William T. Leader
*Attorney, Agent, or Firm*—John Forrest; Jacob Shuster

[57]     ABSTRACT

The organic coating deposited on a metallic substrate is quantitatively evaluated by measurement of electrical signals through an electrochemical cell having an electrode separated from the deposited coating by a porous pad within which a liquid medium is absorbed. Quality determining parameters of the coating are rapidly calculated through a data processor to which electrical current and phase shift measurements are fed together with data from the electrochemical cell. The method may be used to evaluate the quality of the coating on the steel hull of a marine vessel exposed to seawater.

9 Claims, 1 Drawing Sheet

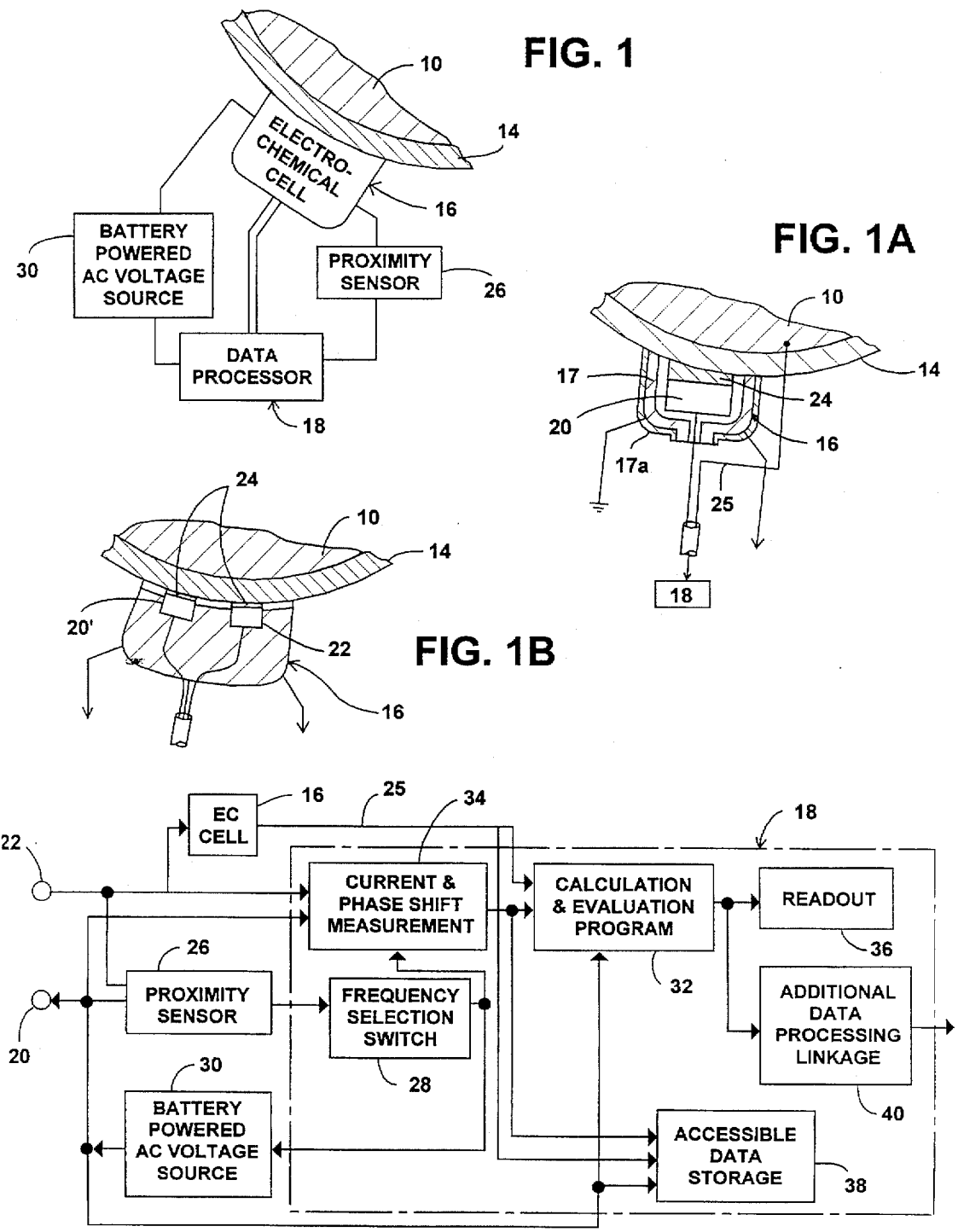

COATING EVALUATION SYSTEM

The present invention relates generally to the evaluation of organic coatings deposited on a metallic substrate surface during exposure to a liquid medium.

BACKGROUND OF THE INVENTION

Various techniques have been utilized and/or proposed for monitoring coatings, including electrochemical impedance spectroscopy techniques through which the status of a coating is determined from various measurement parameters related to electrical impedance of the coating being monitored. Such techniques involve a considerable amount of time to perform measurement and calculation functions with respect to any substantial test surface area on which the coating is deposited. Where no electrical connection to the substrate can be made for measurement purposes, a sensor head having electrodes positioned adjacent to the test surface and spaced therefrom by an air gap has been proposed for determination of coating dielectric loss factors.

As to use of a system for measurement and quality evaluation of a coating from its electrical impedance, U.S. Pat. No. 5,373,734 to Shih et al. is also relevant. Such system is however restricted to use of a container cell, three separate electrodes (one of which having a test surface) and a potentiostat, involved in the performance of the measurement and quality evaluation functions.

It is therefore an important object of the present invention to provide a system for monitoring and evaluation of an organic coating deposited on a relatively large test surface of a metallic substrate (such as the steel hull of a marine vessel) before or after its exposure to a liquid medium such as seawater. In connection with the latter objective, it is a further object to enable more rapid measurement and data calculation with respect to the coating being monitored under the conditions involved.

SUMMARY OF THE INVENTION

In accordance with the present invention, a portable unit including an electrochemical cell and data processor is provided for evaluation of a coating deposited on a test surface of a large metallic substrate, such as the steel hull of a marine vessel before or after exposure to seawater as the liquid medium. At least one electrode within the electrochemical cell is associated with the portable unit conducts electrical current from a low ac voltage source to and from the substrate through the coating. Such electrode within the electrochemical cell is spaced from the coating by a porous separator within which a liquid medium is absorbed and retained. The electrical current and its phase shift by the coating being monitored is measured during each measurement cycle to provide for short term calculation of coating impedance and related parameters by the data processor from which coating quality readouts are obtained. Separately spaced portions of the substrate test surface so monitored are evaluated through sequential measurement cycles during which the portable unit is selectively positioned on the coated substrate with the electrode and the porous separator pressed against the coating.

BRIEF DESCRIPTION OF THE DRAWING FIGURES

A more complete appreciation of the invention and many of its attendant advantages will be readily appreciated as the same becomes better understood by reference to the following detailed description when considered in connection with the accompanying drawing wherein:

FIG. 1 is a partial section view and schematic block diagram illustrating an installational arrangement for the system of the present invention;

FIG. 1a is a section view through the electrochemical cell diagrammed in FIG. 1, in accordance with one embodiment;

FIG. 1b is a section view through the electrochemical cell in accordance with another embodiment; and FIG. 2 is a more detailed block diagram of the system depicted in FIG. 1.

DETAILED DESCRIPTION OF PREFERRED EMBODIMENTS

Referring now to the drawing in detail, FIG. 1 partially illustrates a metallic substrate 10, such as the steel hull of a marine vessel which will be exposed to seawater as a liquid medium. To minimize its exposure to seawater, an organic polymer coating 14 is deposited on the metallic substrate 10. Such deposited coating 14 is to be non-destructively evaluated pursuant to the present invention by means of an electrochemical impedance technique involving use of an electrochemical cell 16 and a data processor 18 as diagrammed in FIG. 1.

The electrochemical cell 16 is of a type generally known in the art used for example to monitor the presence and quantity of hydrogen absorbed within a metal. According to the embodiment shown in FIG. 1a, the cell 16 attached to the organic polymer coating 14 and electrically connected to the metallic/conductive substrate 10, has a single electrode 20 therein which is electrically insulated from the housing 17 of the cell 16 and spaced from the organic polymer coating 14 by a porous separator 24 which has been wetted with seawater or any available aqueous media such as potable water, brackish water or a salt (NaCl) solution. Such a configuration requires a direct electrical connection 25 from the data processor 18 to the conductive substrate 10 as shown in FIG. 1a. The cell housing 17 may be fabricated from an electrically inert substance such as a thermoplastic or thermoset polymer, and may include an electronically conductive material as an outer shell 17a connected to electrical ground to assist in minimizing the inclusion of stray electrical signals or electrical noise which may interfere with an accurate electrical signal subsequently treated by the data processor 18.

FIG. 1b shows another embodiment in which cell 16 is associated with an electrode 20' through which a low ac voltage is applied to the substrate 10 through the coating 14 and a counterelectrode 22 through which electrical current is returned to the cell 16, phase shifted by the coating 14. The cell 16 with associated electrodes 20' and 22 connected to the data processor 18 may be held in a measuring position connected to a proximity sensor 26 and battery powered AC voltage source 30 while pressed onto a test surface of the substrate 10 by any suitable means presently known in the art including for example magnets and/or suction cups, or simply hand held. In accordance with the present invention, the electrodes 20' and 22 when held in position on the substrate are spaced from the coating 14 by porous pad separators 24 within which the seawater is absorbed and retained in order to achieve rapid measurements. By utilizing a porous pad separator 24 that is significantly large in area as compared to its thickness, other fluids such as potable water or brackish water will be as effective as seawater.

The data processor 18 could be either a portable microprocessor unit held externally of and electrically connected by a flexible cord to the electrochemical cell or enclosed in a common casing therewith and internally linked thereto electrically as diagrammed in FIG. 2. The proximity sensor 26 is arranged to detect the operative positioning of the cell 16 relative to the test surface of substrate 10 in order to enable the data processor 18 for evaluation of the coating 14 deposited thereon. Coating evaluation is based on data obtained by application of electrical energy at a frequency above a certain level through cell 16 when properly positioned in the substrate 10. Toward that end, the proximity sensor 26 is connected to a frequency selection switch 28 in the data processor 18 controlling generation of a low ac voltage by a battery powered AC voltage source 30 above the requisite frequency level. Accordingly, under control of the frequency selection switch 28, which is of a rotary or digital type well known in the art, an accumulation of data is initiated in response to applications of the low ac voltage from source 30 of less than 10 mv to the substrate 10 through electrode 20 at a high frequency equal to or above 10,000 Hz. A good quality organic coating having an electrical impedance, usually above 1000 ohms may thereby be identified through a programmed calculation and evaluation section 32 of the data processor 18 to which the electrode 20 in cell 16 is connected through the sensor 26 and switch 28 for data measurement purposes on a short term basis to accommodate repeated measurements at different locations on the substrate 10. Measurement data related to ac current conducted to the substrate 10 through electrode 20' and its phase shift by coating 14 as reflected by return current from electrode 22 as shown in FIG. 1b is also obtained through a current and phase shift measurement section 34. Such measurement data is fed to the calculation and evaluation section 32 as diagrammed in FIG. 2.

Calculations are performed within section 32 of the data processor 18 pursuant to its calculation and evaluation program based on the supply of ac current from low voltage source 30 at the high frequency (f) aforementioned, where $$Z = \frac{1}{2\pi f C}$$

and (C) is the capacitance of coating 14 reflecting its dielectric characteristic (ε). The capacitance (C) is related to the dielectric characteristic (ε) by the formula $$C = \frac{\varepsilon \varepsilon^0 A}{t},$$

where $\varepsilon^0$ is the dielectric constant of a vacuum, (A) is the area of the test surface of substrate 10 being measured and (t) is the thickness of the coating 14. Based on the type of coating 14 to be evaluated, the appropriate high frequency at or above 10,000 Hz is selected through switch 28 in order to restrict correspondingly the signal generating function of voltage source 30 and the current and phase shift measurement function of section 34 from which programmed calculation and evaluation functions are performed by section 32 of the data processor 18. Readout of coating quality is thereby obtained through section 36 of the data processor, also having an accessible data storage section 38 and interrelating linkages as diagrammed in FIG. 2, including a hardware section 40 for linkage to other conventional PC computer hardware providing additional data analysis capabilities.

The coating evaluation system as hereinbefore described, performs rapid calculations of the impedance (Z) and related parameters of the coating 14 through sections 32 and 34 of the data processor 18 for storage in section 38 and digital display through readout section 36. The impedance related parameters may include current phase shift value (n) as well as coating capacitance (C) and thickness (t) as aforementioned, restricted by signal frequency selection through switch 28 to certain types of coatings corresponding to the organic polymers deposited on the hull of a marine vessel before or following exposure to seawater. From such parameter values displayed by the readout section 36 of the data processor, coating quality related to degree of damage and/or potential corrosion of the underlying substrate is deduced.

Rapid readout of the aforementioned coating parameters during separate measurement cycles for different sampled portions of the underlying substrate test surface provide a basis for a report mapping coating quality. Such mapping report on coating quality will require sequential displacement of the electrochemical cell 16 along the test surface of the substrate during intervals between measurement cycles under control of the data processor 18.

Obviously, other modifications and variations of the present invention may be possible in light of the foregoing teachings. It is therefore to be understood that within the scope of the appended claims the invention may be practiced otherwise than as specifically described.

What is claimed is:

1. A method for evaluating quality of a coating deposited on a substrate and wetted by seawater during exposure of the substrate thereto, comprising the steps of:

positioning on said substrate an electrochemical cell which comprises a housing, an electrode and a porous medium covering said electrode, said porous medium separating said electrode from the coating;

absorbing and retaining the seawater in said porous medium during said exposure of the substrate thereto;

generating an AC voltage not exceeding 10 mV and applying said AC voltage to said electrode to conduct electrical current at a fixed frequency above 10,000 Hz to the substrate through the coating;

measuring the electrical current and phase shift thereof in response to said conduction through the coating;

calculating a characteristic of the coating from parameters thereof and measurement data obtained from said step of measuring; and extracting a readout of said characteristic which is representative of the quality of the coating.

2. The system as defined in claim 1 wherein the coating is an organic material.

3. The system as defined in claim 2 wherein the substrate is metallic material.

4. The system as defined in claim 3 wherein the substrate is a steel hull of a marine vessel.

5. The method as defined in claim 4 wherein said parameters of the coating include electrical capacitance and thickness.

6. The method as defined in claim 5 wherein said method includes: displacement of the electrode between plural test surface portions of the substrate at which said steps of generating measuring and calculating are performed to provide a map of the coating quality through said step of extracting a readout.

7. The system as defined in claim 1 wherein the substrate is a steel hull of a marine vessel.

8. The method as defined in claim 1 wherein said method includes: displacement of the electrode between plural test surface portions of the substrate at which said steps of generating measuring and calculating are performed to provide a map of the coating quality through said step of extracting a readout.

9. The method as defined in claim 1 wherein said parameters of the coating include electrical capacitance and thickness.

* * * * *